(12) United States Patent
Thompson et al.

(10) Patent No.: US 6,817,227 B2
(45) Date of Patent: Nov. 16, 2004

(54) ABOVEGROUND LEAK DETECTION SYSTEM FOR DETECTING SUB-SURFACE FLUID LEAKS FROM FLUID CONTAINING VESSELS

(75) Inventors: Glenn M. Thompson, Tucson, AZ (US); O. Daniel Evans, Tucson, AZ (US)

(73) Assignee: Praxair Technology, Inc., Danbury, CT (US)

( * ) Notice: Subject to any disclaimer, the term of this patent is extended or adjusted under 35 U.S.C. 154(b) by 105 days.

(21) Appl. No.: 10/095,161

(22) Filed: Mar. 11, 2002

(65) Prior Publication Data

US 2003/0167861 A1 Sep. 11, 2003

(51) Int. Cl.$^7$ ................................................. G01N 1/00
(52) U.S. Cl. .................. 73/40.7; 73/864.31; 73/863.21; 73/864.34
(58) Field of Search ............................ 73/40.7, 863.21, 73/864.31, 864.34, 864.71, 864.72, 864.74, 865.8, 863.31, 863.33

(56) References Cited

U.S. PATENT DOCUMENTS

| | | | |
|---|---|---|---|
| 3,420,091 A | * 1/1969 | Franklin | 73/23.2 |
| 4,709,577 A | 12/1987 | Thompson | 73/40.7 |
| 4,725,551 A | 2/1988 | Thompson | 436/3 |
| 4,754,136 A | 6/1988 | Blakely | 250/301 |
| 4,982,616 A | * 1/1991 | Koch et al. | 73/864.81 |
| 5,046,353 A | 9/1991 | Thompson | 73/40.7 |
| 5,048,324 A | 9/1991 | Thompson | 73/40.7 |
| 5,076,728 A | 12/1991 | Golding | 405/128 |
| 5,355,739 A | * 10/1994 | Cooper et al. | 73/864.73 |
| 5,447,055 A | 9/1995 | Thompson et al. | 73/49.2 |
| 5,587,538 A | * 12/1996 | Bratton | 73/863.33 |
| 5,922,974 A | * 7/1999 | Davison et al. | 73/864.74 |

\* cited by examiner

*Primary Examiner*—Robert Raevis
(74) *Attorney, Agent, or Firm*—David M. Rosenblum

(57) ABSTRACT

An apparatus and method for sampling sub-surface soil gas samples and detection of distinctive chemical tracer compounds in the soil gas samples employing an aboveground sampling apparatus. The aboveground sampling apparatus does not include any device that penetrates the soil surface or man-made structures imposed upon the soil surface. Rather, the above-ground sampling apparatus evacuates soil gas samples through the soils surface or through mad-made structures imposed upon the soil surface, such as asphalt or concrete, and passes the soil gas sample through an adsorbent bed containing adsorbent material specific for the distinctive chemical tracer compounds.

16 Claims, 4 Drawing Sheets

US 6,817,227 B2

ABOVEGROUND LEAK DETECTION SYSTEM FOR DETECTING SUB-SURFACE FLUID LEAKS FROM FLUID CONTAINING VESSELS

BACKGROUND OF THE INVENTION

The present invention relates generally to leak detection systems for detecting fluid leaks from fluid storage tanks using distinctive tracer compounds to provide detectable components in a fluid leak from the tank. The present invention also relates to a system for soil gas sampling, analysis and reporting to determine the presence and magnitude of a fluid leak from a fluid storage tank. More particularly, the present invention relates to an aboveground system that collects sub-surface soil gases for analysis without the need to penetrate the soil. The present invention exhibits utility whether used to detect leaks in underground fluid storage tanks, aboveground fluid storage tanks or in fluid transfer pipelines. For purposes of clarity all such vessels shall be referred to as fluid storage tanks. The fluid stored in the fluid storage tank may be either a liquid, such as gasoline, or may be a gas, such as methane, natural gas, butane, propane or the like.

The present invention further provides a tracer leak detection method that relies upon the addition of a highly volatile liquid chemical to the fluid contained within the fluid storage tanks. These tracer chemicals provide a unique and identifiable analytical signature. This signature is then used to detect and localize very small leaks from fluid storage tanks. When a leak occurs in the fluid storage tank, the leaking fluid will contain a quantity of the tracer chemical. The tracer escapes from the fluid by vaporization and disperses into the surrounding soil by molecular diffusion. Soil gas samples are collected from the subsurface soil area by withdrawing a volume of soil gas through the surface of the soil, including any man-made surfaces thereupon, e.g., concrete, asphalt, etc. Gas chromatography is employed on the collected soil gas samples to reveal the presence of the gas phase tracer, if any is present in the collected sample. The selection of tracer is important to insure that it provides a unique signature for gas chromatography.

The types of tracer chemicals useful in the present invention are more fully described in U.S. Pat. Nos. 4,725,551 and 4,709,557 issued to Glenn Thompson (hereinafter the "551 Patent" and the "'557 Patent", respectively) the disclosures and teachings of which are expressly incorporated herein. Ideally, the selected tracer is normally a highly volatile organic tracer having a boiling point in the range of about −72° C. to about 150° C., with the preferred compounds being of the group known as fluorocarbons.

A wide variety of different soil gas sampling leak detection methodologies are known. Common to each of these methods is the provision of some means for collecting soil gas samples. For example in each of the '551 and '557 patents a sampling probe is vertically disposed in the backfill material surrounding an underground tank. The sampling probe has a plurality of apertures to permit soil gases to enter the probe for subsequent evacuation. It is also well known to employ carbon adsorbents in the sampling probe to collect hydrocarbons or tracer chemicals for subsequent collection by desorbing from the carbon and analysis of the desorbed gas. Similarly, U.S. Pat. No. 4,754,136 discloses that a neutron backscatter gauge may be lowered into the sampling probe to determine whether the probe contains volatile organic material indicative of a leak from a fluid storage tank. A positive neutron back scatter reading is verified by running a gas chromatogram on a soil gas sample collected from the sampling probe and comparing the chromatographic signature with the known material in the fluid storage tank.

Each of these leak detection systems require that a soil gas sample be taken from the sub-surface sampling probe then analyzed on a gas chromatograph. Each of these systems require that some type of probe be inserted into the sub-surface soil region proximate to the fluid containing tank in order to sample soil gases for leak detection. None of these systems, however, provide a method or apparatus for sampling soil gases for leak detection that does not require insertion of probes, housings or other devices for collection of the soil gas samples. Moreover, none of these conventional systems offer an apparatus and method for collecting sub-surface soil gas samples from above the surface of the soil. It has been found desirable, therefore, to provide an apparatus and method for collecting sub-surface soil gas samples above ground by evacuating soil gases from the soil surface, passing the gas sample through a filter and onto an adsorbing bed specific for adsorbing distinctive tracer chemicals present in the sub-surface fluid storage tank.

SUMMARY OF THE INVENTION

Underground and above-ground fluid storage tanks and fluid pipelines interconnecting such storage tanks with dispensing pumps typically contain environmentally hazardous chemicals, such as hydrocarbon fuels or solvents. Some portion or all of the tank and pipelines often reside in the sub-surface soil that is covered by a man-made material, such as concrete or asphalt. Conventional leak detection systems require sub-soil insertion of a field of probes or wells that penetrate into the underground area proximate the pipelines or fluid storage tanks. Soil gas samples are obtained either by evacuating samples from the probes or wells or by adsorbing soil gases onto an adsorbent bed placed within the probe or well and removing the adsorbent bed from the probe or well for analysis. Where the fluid storage tanks and/or the pipelines are located in regions covered by man-made materials, insertion of probes and/or wells into the sub-surface soil area is difficult, expensive and labor-intensive.

It is, therefore, a principal object of the present invention to provide a system for determining whether a fluid storage tank is leaking without the need to penetrate into the sub-surface soil area. This objective is achieved by providing an apparatus which is usable above-ground for sampling sub-surface soil gas samples for analysis of the presence of a distinctive chemical tracer present introduced only into the fluid storage tank. The present invention comprises an apparatus that includes a sled base consisting of a planar quadrilinear, or ski shaped plate (hereafter called the "plate") having an upturned leading edge and having an annular opening passing through the plate and centrally positioned on the plate, a tubular manifold in fluid flow communication with the annular opening and passing upwardly therefrom, to a sample collection means. The sample collection means is comprised of a vacuum pump, a filter, and a sample tube containing an adsorbent material specific for the distinctive tracer introduced into the fluid contained within the fluid storage tank. A flow meter, to enable monitoring the amount of sample that passes through the adsorbent tube, may be used at the out let of the sample collection means. A pressure gauge or vacuum gauge placed between the pump and the adsorbent tube may also be used to monitor the rate of airflow through the adsorbent tube.

The sample collection means may be mounted on the plate, in which case it is connected directly to the opening in the central portion of the plate. Or, the sample collection means may be mounted remotely from the plate, either carried in a backpack or mounted in a vehicle, in which case the sample collection means is connected to the opening in the central portion of the plate by means of an appropriate length of small diameter tubing sufficient to span the distance from the plate to the sample collection means. Also, if the sample collection means is mounted remotely from the plate, it may be connected directly to a gas chromatographic means for analysis of the chemical tracer. If the sample collection means is not connected directly to the gas chromatograph, then the sample tubes are removed manually from the collection apparatus and manually connected to the gas chromatograph for analysis.

These and other objects, features and advantages of the present invention will become more apparent to those skilled in the art from the following more detailed description of the preferred embodiments of the invention taken with reference to the accompanying drawings.

DETAILED DESCRIPTION OF THE PREFERRED EMBODIMENTS

Figure 1:
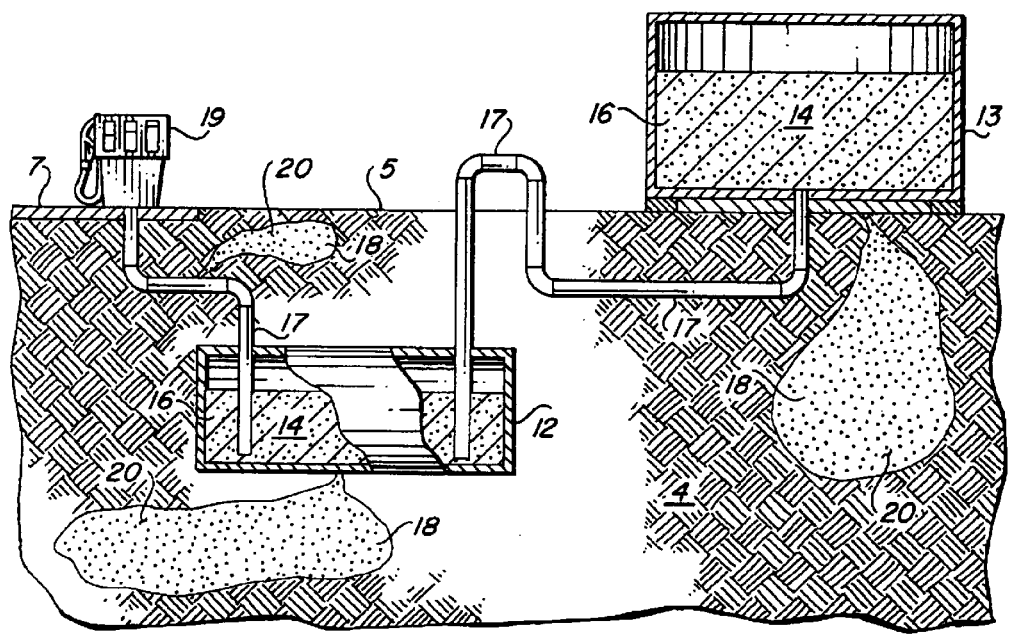
FIG. 1 is a diagrammatic view of a tank farm including aboveground and underground fluid storage tanks and fluid pipelines.

The inventive system for aboveground sampling of subsurface soil gases for detection of distinctive chemical tracer signatures therein is illustrated with reference to the accompanying drawings. With specific reference to FIG. 1 there is shown an exemplary fluid storage tank farm. An underground fluid storage tank 12 placed within the sub-surface region and is supported by an earthen material 4, such as a backfill of soil, pea gravel or sand. An aboveground fluid storage tank 13 is constructed onto the soil and typically placed onto a sand bed. A plurality of fluid pipelines 17 is disposed either in the subsurface region or penetrates the surface and resides above the earthen surface. A fluid 14, such as a gas or liquid, is contained within the fluid storage tanks and pipelines 12, 13, 17 and is dispensed therefrom by pumps 19.

A tracer chemical 16 is introduced into the fluid 14 within fluid storage tanks 12, 13 or pipelines 17. Preferred tracer chemicals are described in greater detail in the Thompson '551 and '557 patents that are expressly incorporated by reference thereto. Ideally, the selected tracer is normally a highly volatile organic tracer having a boiling point in the range of about −72° C. to about 150° C., with the preferred compounds being of the group known as fluorocarbons.

A fluid leak 18 from the fluid storage tanks 12, 13 or the pipelines 17 into the earthen material 4, causes the tracer chemical 16 to also leak into the earthen material 4, volatilize in the subsurface soil and disperse in a tracer plume 20 within the earthen material 4, thereby providing a unique detectable component in the earthen material 4.

Figure 2:
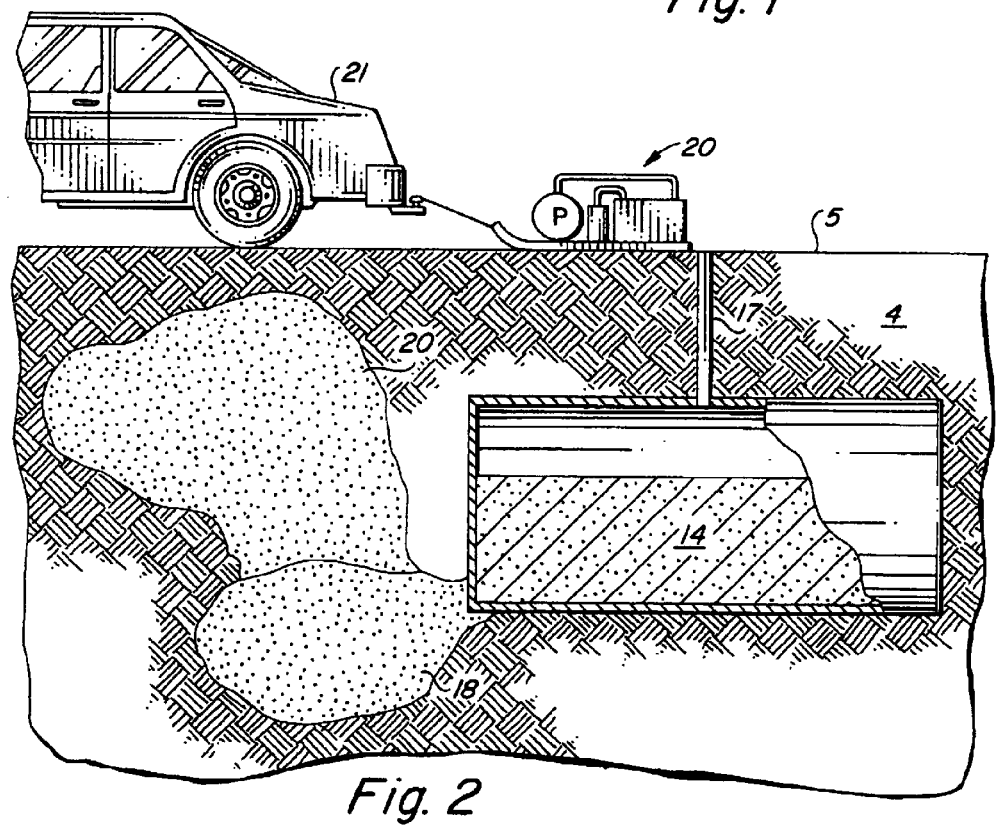
FIG. 2 is a diagrammatic view of the present invention being drawn by a motor vehicle proximate to an underground fluid storage tank.
Figure 3:
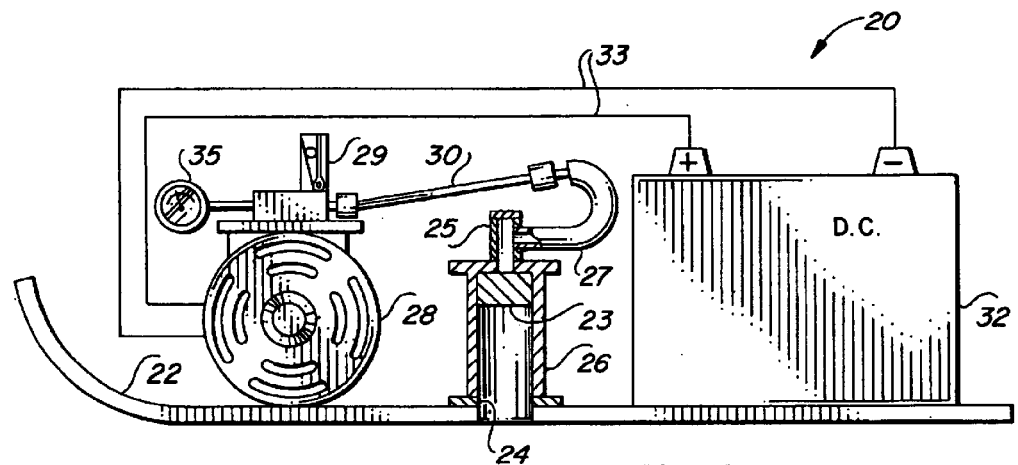
FIG. 3 is a side elevational view of the soil gas sampling apparatus with the sample collection means mounted directly on the plate in accordance with the present invention.

The inventive soil gas collection apparatus 20 is depicted generally in FIG. 2, in use, and more specifically in FIG. 3. Soil gas collection apparatus 20 consists generally of a planar base member 22 having an upper surface and a lower surface and at least one aperture 24 passing through the planar base member 22 and communicating between the upper and lower surfaces thereof. The planar base member 22 is preferably fabricated of a highly durable material, such as steel, carbon fiber materials or plastics. It is preferable that the planar base member be configured to have a sled-like geometry with an upturned leading edge that permits the base member 22 to more readily traverse uneven surfaces. A protective cover may also be added to prevent brush or other material from catching or settling on the pump, tubing or other mechanisms on the planar base member when the apparatus 20 is being drawn through vegetated areas. A tether (not shown) is preferably attached to a leading section of the planar base member 22 so that the apparatus 20 may be moved by attachment to a motor vehicle 21 or by a human being.

At least one intake manifold 26 is connected in fluid flow communication with the at least one aperture 24 and is upstanding from the upper surface of the planar base member 22. The at least one intake manifold 26 may be connected to the planar base member by suitable means, such as threaded couplings, interference couplings or welding, or it may be formed as an integral monolithic component with the planar base member such as by casting or stamping. A pump 28 is mounted on the upper surface of the planar base member 22 and is connected in fluid flow communication with the at least one intake manifold 26 by tubing 27. A filter medium 23 is preferably disposed within the at least one intake manifold 26 or in-line with the fluid flow through the at least one intake manifold 26 to filter particulates from the fluid flow. Interposed in-line between the at least one intake manifold 26 and the pump 28 is at least one sample tube 30 containing an adsorbent material specific for at least one of the distinctive chemical tracer compounds introduced into the fluid storage tanks 12, 13 or the pipelines 17. Sample tube 30 is removable and connectable to a gas chromatograph (not shown) for purposes of desorbing any adsorbed tracer compounds for quantification and analysis. Tubing 27 is connected at one end thereof, to a connector 25 mounted on the at least one intake manifold 26, and at a second end to the sample tube 30. Sample tube 30 is connected at a second end thereof to the pump 28. Pump 28 is driven by a power source 32 that supplies electrical power to the pump via electrical connectors 33. A flowmeter 29 is also preferably provided on the exhaust side of the sample tube 30 to monitor the fluid flow through the sample tube 30 and ensure that sufficient volumes of fluid flow are being sampled.

In accordance with the present invention, the pump 28, at least one intake manifold 26, connector 25, tubing 27, sample tube 30 and power supply 32 are all mounted onto the planar base member 22. Those skilled in the art will understand and appreciate, however, that the power supply 32, the pump 28 and even the at least one sample tube 30 may be carried on a structure separate from the planar base member 22, while still being in fluid flow communication and electrical communication therewith.

In use, the soil collection apparatus 20 may be attached to a motor vehicle 21 or drawn by a human being (not shown) and drawn across the surface of the subsurface region field to be tested. The surface 5 of the subsurface region field may be a earthen surface or may be covered by a porous man-made material 7, such as concrete or asphalt. Porous man-made materials permit permeation and diffusion of the chemical tracer compounds into and through the man-made materials and permit detection of the chemical tracer compounds therethrough.

Soil gas samples are typically analyzed by gas chromatography. Using gas chromatography it is possible to analyze whether the distinctive chemical tracer compound is present in the soil gas sample, and, if so, its concentration level in the sample.

Figure 4:
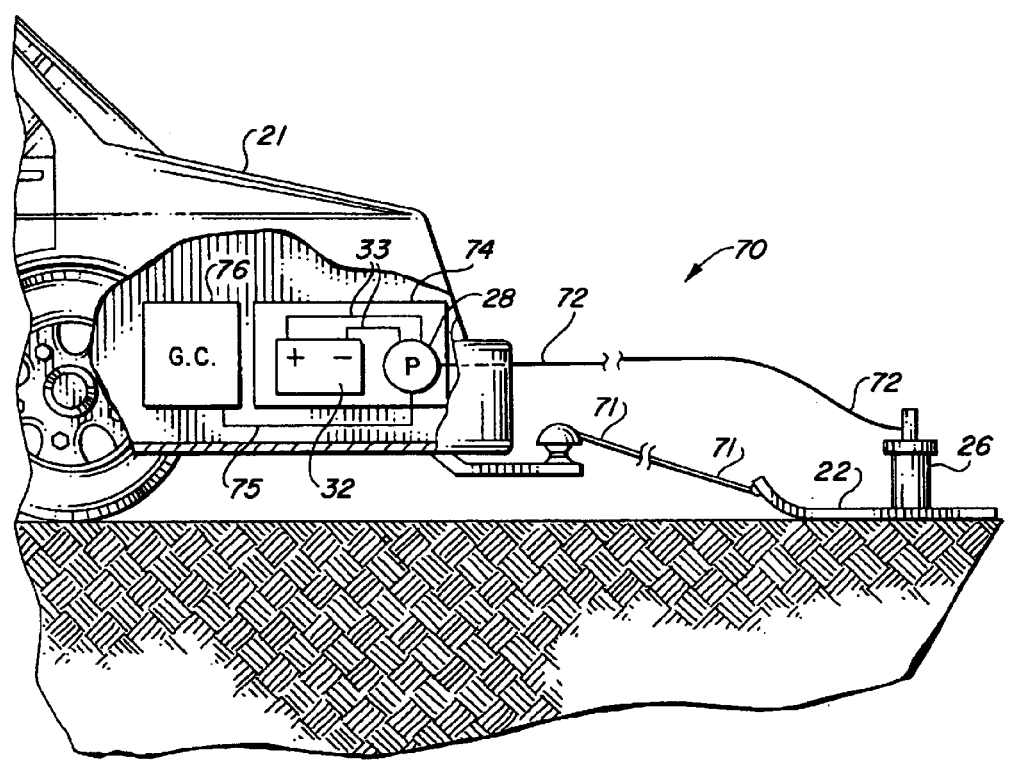
FIG. 4 is a side elevational view of the soil gas sampling system of the present invention with the sample gas collector mounted in a motor vehicle and couple to a gas chromatograph to provide continuous analytical cycling of soil gas samples.

FIG. 4 illustrates an alternative embodiment of the invention 70 in which the planar base member 22 is mounted with at least one intake manifold 26 in fluid flow communication though an opening in the planar base member (not shown) substantially as described above. In accordance with this alternative embodiment of the invention 70, however, the pump 28 and power supply 32, and the electrical connectors 33 are remotely situated from the planar base member 22, such as being mounted on a vehicle 21. The planar base member 22 is tethered via a line 71 secured to the vehicle 21. A fluid conduit 72 communicates between the pump 28 and the at least one intake manifold 26 extends between the vehicle and is preferably also coupled to the line 71. In this configuration, the pump will evacuate a subsurface soil gas sample from the at least one intake manifold 26, withdraw the sample thorough the pump, and feed the sample either directly to a gas chromatograph 76 or may be adsorbed on a sampling tube (not shown) and desorbed for feeding into the gas chromatograph 76. This alternative embodiment 70 permits a continuous cycling of subsurface soil gas samples through the analytical instrument to provide a more "real-time" reading on the tracer levels in the subsurface soil samples.

Figure 5:
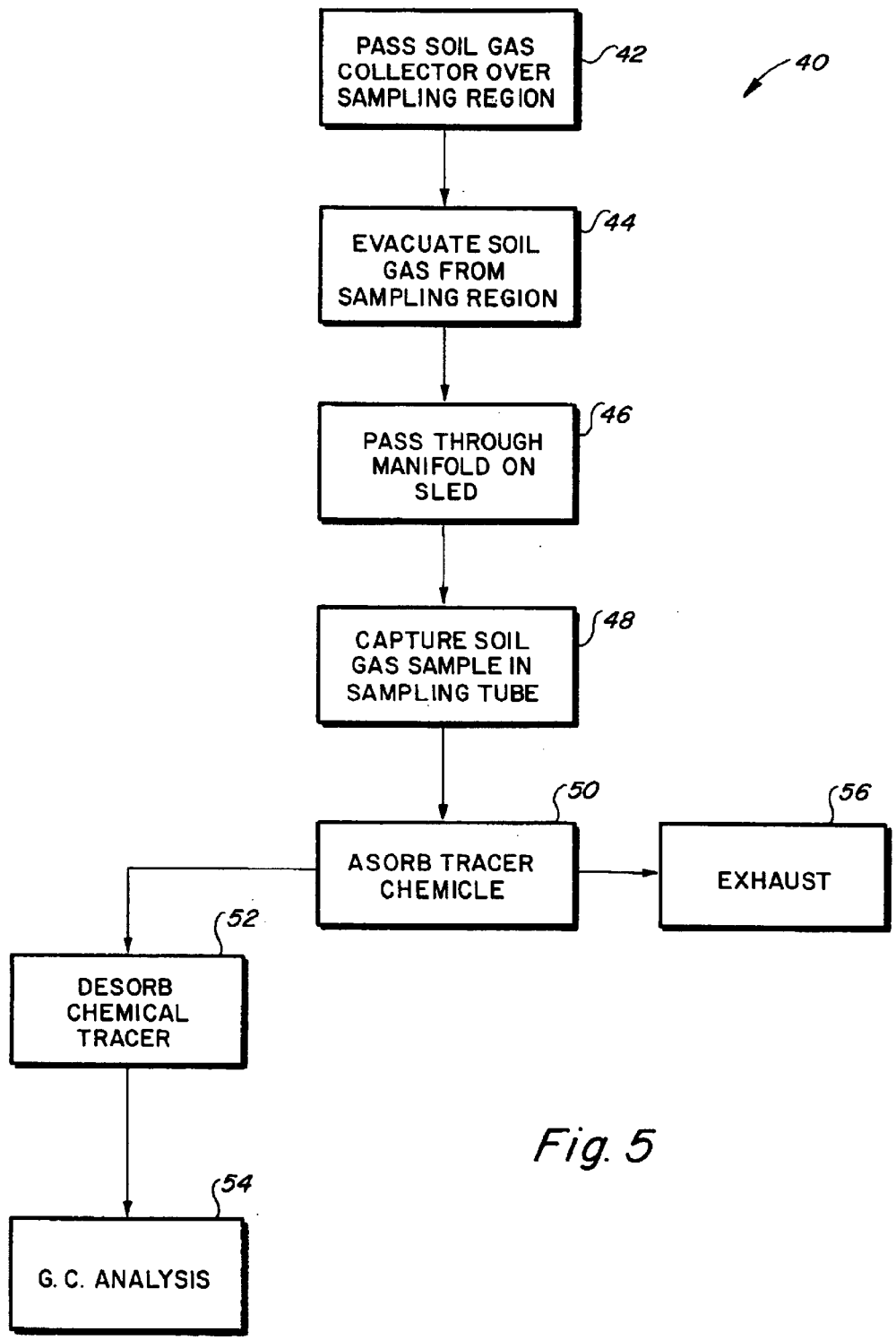
FIG. 5 is a flow diagram illustrating the soil gas sampling method of the present invention.

FIG. 5 illustrates the method 40 for detecting the presence of a distinctive chemical tracer compound, and thus, of a leak in one or more fluid storage tanks or pipelines in accordance with the present invention. First, a soil gas collector, such as described above, is passed over the sampling region in proximity to the storage tanks and pipelines to be tested 42. The soil gas collector is supported by and rests upon the surface of the sampling region, which may consist of earthen material, gravel, concrete, asphalt, sand, or other similar porous material. While the soil gas collector is being passed over the sampling region, soil gas samples are evacuated 44 from the sampling region by drawing the soil gas samples through the surface of the sampling region and into the soil gas collector. The soil gas samples pass through an intake manifold on the soil gas collector 46 and are captured 48 in a sampling tube. Any tracer compound is adsorbed 50 onto an adsorbent material within the sampling tube, and non-adsorbed soil gas is exhausted 56 from the soil gas collector. After completing a sampling run in the sampling region, the sampling tube is disengaged from the soil gas collector and connected to a gas chromatograph where any captured chemical tracer compound is desorbed 52 from the adsorbent material. The desorbed sample is then fed into a gas chromatograph for analysis 54 of the presence and concentration of any distinctive chemical tracer in the sample. If the distinctive chemical tracer is found in the sample, the sample may be correlated to the geographical coordinates of the sample origin and the concentration of the chemical tracer mathematically correlated to quantify a leak rate, based upon concentration in sample volume and known concentration of tracer in known volume of fluid in the storage tank or pipeline.

EXAMPLE 1

A leak test was performed on a 4-mile section of underground pipeline that was believed to be leaking because it had failed a hydrostatic pressure test. The leak was very small and other leak testing methods had failed to locate the leak. The fluid in the pipeline was inoculated with 10 ppb of a first fluorocarbon tracer, Tracer R. A second fluorocarbon tracer, Tracer E, that was distinct from the tracer contained within the pipeline was used as a leak simulation. The Tracer E was released into the soil outside of the pipeline as a means of verifying the performance of the leak detection procedure and as a means of calibration to determine the size of any leaks that were detected. The amount of Tracer E released into the soil was equivalent to the amount of Tracer R that was contained in 10 gallons of fluid from inside the pipeline.

Figure 6:
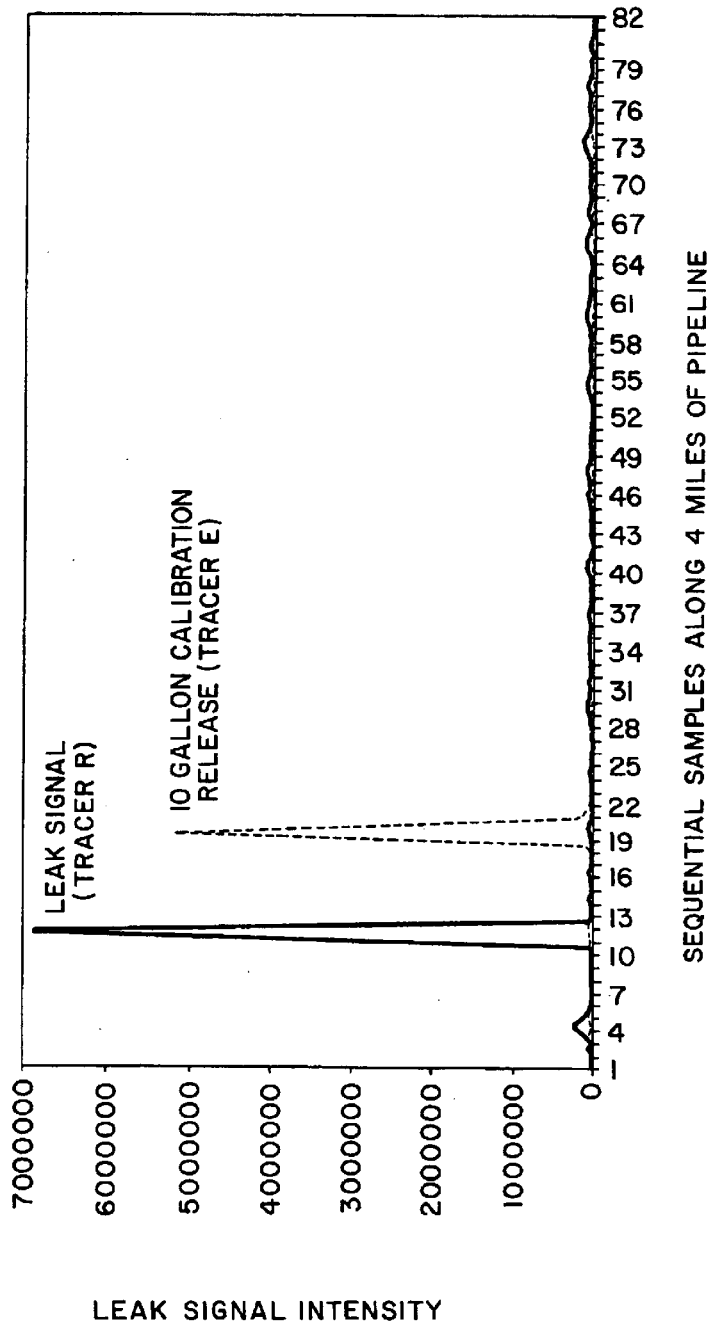
FIG. 6 is a graph illustrating the results of tracer measurement from Example 1, below.

The inventive soil gas collection sled was dragged behind a truck for 4 miles of pipeline over the course of about 5 hours while continuously evacuating soil gas samples from underneath the sled. The sample collection tubes were changed every 260 feet (approximately every 79 meters). A total of 82 samples were collected. The samples were analyzed using gas chromatography and the presence of the tracer from both the pipeline leak and from the simulated leak were verified. The results of the tracer measurements are shown in FIG. 6. By comparing the amount of Tracer R detected from the actual leak with the amount of Tracer E detected from the 10 gallon simulated leak, it can be seen that the real leak was only slightly larger. The real leak appears to have been only 12 or 15 gallons by comparison.

From the foregoing, those skilled in the art will understand that the invention has been fully and fairly described in such a manner as to enable one skilled in the art to practice the invention. While the best mode for practicing the invention has been disclosed, those in the art will understand and appreciate that a wide variety of variations and substitutions may be made in, for example, individual valve and switch selections, connection line materials, tracer selection, tank or pipeline type and operational parameters without departing from the spirit and scope of the present invention.

What is claimed is:

1. Aboveground system for collecting sub-surface soil gases, comprising:

a) a generally planar base member formed of a plate and having an upper surface and a lower surface and at least one aperture passing through the planar base member and extending between the upper surface and the lower surface;

b) at least one fluid flow conduit connected to the at least one aperture passing through the planar base member;

c) a pump communicating with to the at least one fluid flow conduit for drawing a negative pressure therethrough;

d) collection means connected to the pump for collecting soil gases drawn through the at least one aperture in the planar base member, through the at least one fluid flow conduit and into the collection means; and e) at least one adsorbent retained within the collection means and specific for a desired chemical compound present in the subsurface soil gas.

2. The aboveground system according to claim 1, wherein the generally planar base member further comprises a metal sled having an upturned leading edge.

3. The aboveground system according to claim 2, wherein the lower surface of the metal sled is placed in contact with a surface through which a sub-surface soil gas is to be collected.

4. The aboveground system according to claim 1, further comprising a filter member disposed in fluid flow communication between the at least one fluid flow conduit and the pump.

5. The aboveground system according to claim 4, further comprising an electrical power source for supplying electrical power to the pump.

6. The aboveground system according to claim 5, wherein the pump and the collection means are mounted onto the generally planar base member.

7. The aboveground system according to claim 1, wherein the at least one adsorbent further comprises an adsorbent specific for a chemical tracer compound selected from the group consisting of fluorocarbons having a boiling point in the range of about −72° C. to about 150° C. under standard temperature and pressure conditions.

8. The aboveground system according to claim 7, wherein the at least one adsorbent further comprises an adsorbent specific for a chemical tracer compound selected from the group consisting of fluorocarbons.

9. A method for detecting distinctive chemical tracer compounds in sub-surface soil gas samples comprising the steps of:
  a) passing a soil gas collector immediately above and in physical contact with an upper surface of the sub-surface soil region to be tested;
  b) evacuating a soil gas sample from the sub-surface soil region, through the upper surface thereof, and into the soil gas collector;
  c) collecting the soil gas sample; and
  d) analyzing the soil gas sample for the presence of a distinctive chemical tracer compound therein.

10. The method according to claim 9, wherein step (a) further comprises the step of passing over and in contact with an earthen region to be tested, a planar sled member having at least one aperture passing therethrough a communicating between an upper surface and a lower surface of the planar sled member, at least one fluid flow conduit connected to the at least one aperture, a pump mounted on the planar sled member connected in fluid flow communication to the at least one fluid flow conduit, and collection means having at least one adsorbent specific for at least one distinctive chemical tracer compound.

11. The method according to claim 10, wherein step (b) further comprises the step of pumping, with the pump, a soil gas sample from the earthen region through the at least one aperture in the planar sled member and the at least one fluid conduit and onto the at least one adsorbent.

12. The method of claim 9, further comprising the step of doping fluid contained within at least one fluid vessel selected from the group consisting of aboveground fluid storage tanks, underground fluid storage tanks, and fluid pipelines with at least one distinctive chemical tracer compound.

13. The method of claim 12, wherein the step of doping with at least one distinctive chemical tracer compound further comprises the step of selecting the at least one distinctive chemical tracer compound from the group consisting of fluorocarbons.

14. The method of claim 12, wherein the at least one distinctive chemical tracer compound has a boiling point in the range of about −72° C. to about 150° C. under standard temperature and pressure conditions.

15. The method of claim 12, wherein the at least one distinctive chemical tracer compound has a boiling point less than the boiling point of the fluid doped with the chemical tracer compound.

16. The method of claim 12, wherein the at least one distinctive chemical tracer compound is selected from the group consisting of fluorocarbons.

* * * * *

UNITED STATES PATENT AND TRADEMARK OFFICE
CERTIFICATE OF CORRECTION

PATENT NO. : 6,817,227 B2
DATED : March 11, 2002
INVENTOR(S) : Thompson et al.

It is certified that error appears in the above-identified patent and that said Letters Patent is hereby corrected as shown below:

Column 6,
Line 67, delete "subsurface" and insert -- sub-surface --

Signed and Sealed this

Fifth Day of April, 2005

JON W. DUDAS
*Director of the United States Patent and Trademark Office*